US012564729B2

(12) United States Patent
Brinkmann

(10) Patent No.: US 12,564,729 B2
(45) Date of Patent: Mar. 3, 2026

(54) DEVICE FOR TREATING BIOLOGICAL TISSUE

(71) Applicant: Medizinisches Laserzentrum Lübeck GmbH, Lübeck (DE)

(72) Inventor: Ralf Brinkmann, Lübeck (DE)

(73) Assignee: Medizinisches Laserzentrum Lübeck GmbH, Lübeck (DE)

( * ) Notice: Subject to any disclaimer, the term of this patent is extended or adjusted under 35 U.S.C. 154(b) by 285 days.

(21) Appl. No.: 18/547,593

(22) PCT Filed: Feb. 15, 2022

(86) PCT No.: PCT/EP2022/053660
§ 371 (c)(1),
(2) Date: Aug. 23, 2023

(87) PCT Pub. No.: WO2022/179888
PCT Pub. Date: Sep. 1, 2022

(65) Prior Publication Data
US 2024/0299768 A1 Sep. 12, 2024

(30) Foreign Application Priority Data
Feb. 23, 2021 (EP) ..................................... 21158631

(51) Int. Cl.
*A61N 5/06* (2006.01)
*A61B 17/00* (2006.01)
*A61B 18/00* (2006.01)

(52) U.S. Cl.
CPC .. *A61N 5/0613* (2013.01); *A61B 2017/00181* (2013.01); *A61B 2018/00642* (2013.01);
(Continued)

(58) Field of Classification Search
CPC .......... A61N 5/0613; A61N 2005/0626; A61B 2017/00181; A61B 2018/00642; A61B 2018/00761; A61B 2018/0088
See application file for complete search history.

(56) References Cited

U.S. PATENT DOCUMENTS 10,806,513 B2 * 10/2020 Rao ...................... A61B 18/203
2019/0128804 A1 * 5/2019 Ushida ................ A61L 27/3612

FOREIGN PATENT DOCUMENTS

DE 102010018679 A1 11/2011
EP 1279385 A1 1/2003
(Continued)

OTHER PUBLICATIONS

Brinkmann Ralf, Translation of WO-2010028822-A1, 2010 (Year: 2010).*
(Continued)

*Primary Examiner* — Adam Z Minchella
(74) *Attorney, Agent, or Firm* — Alix, Yale & Ristas, LLP

(57) ABSTRACT

The invention relates to a device for treating biological tissue (19), comprising a light source (14) for sending a plurality of light pulses (15) to the tissue (19) within a treatment time period (31) in order to cause the tissue (19) to vibrate. The device comprises a vibration sensor (21), which senses the amplitude of a vibration (22) of the tissue (19) brought about by the light source (14). A control unit (16) calculates a relative value (30) by putting a current measurement value (27) of the amplitude in a ratio with an initial measurement value (26) of the amplitude. The control unit (16) processes the relative value (30) in order to generate a control signal for the light source (14).

15 Claims, 3 Drawing Sheets

(52) U.S. Cl.
CPC .............. *A61B 2018/00761* (2013.01); *A61B 2018/0088* (2013.01); *A61N 2005/0626* (2013.01)

(56) References Cited

FOREIGN PATENT DOCUMENTS

| WO | WO-2010028822 A1 * | 3/2010 | ............. A61F 9/008 |
| WO | 2018209118 A2 | 11/2018 | |

OTHER PUBLICATIONS

English Translation of International Preliminary Report on Patentability for International Application No. PCT/EP2022/053660 filed on Feb. 15, 2022, Date of Mailing: Sep. 7, 2023; 7 pgs.

Ingo Ulrik Teudt et al, "Acoustic Events and Optophonic Cochlear Responses Induced by Pulsed Near-Infrared Laser", IEEE Transactions on Biomedical Engineering, IEEE Service Center, Piscataway, NJ, USA, vol. 58, No. 6, Jun. 1, 2011 (Jun. 1, 2011), pp. 1648-1655, XP011408389, DOI: 10.1109/TBME.2011.2108297, ISSN:0018-9294, 8 pgs.

Muqun Yang et al, "Photoacoustic effect invokes auditory response in infrared neuron stimulation", Journal of Innovative Optical Health Sciences, Singapore vol. 12, No. 1, XP05582986, DOI: 10.1142/S1793545818500402, ISSN:1793-5458, Jan. 1, 2019 (Jan. 1, 2019), pp. 1850040-1-1850040-8, 8 pgs. Retrieved from the Internet: URL:https://www.worldscientific.com/doi/pdf/10.1142/S1793545818500402.

Gentiana I. Wenzel, et al, "Green laser light activates the inner ear", Journal of Biomedical Optics, vol. 14, No. 4, 0044007 (Jul./Aug. 2009), ISSN: 1083-3668, pp. 044007-1-044007-6, 6 pgs. Downloaded From: https://www.spiedigitallibrary.org/journals/Journal-of-Biomedical-Optics on Jul. 10, 2023.

PCT International Search Report and Written Opinion for International Application No. PCT/EP2022/053660 filed on Feb. 15, 2022, Date of Mailing: May 3, 2022, 13 pgs.

* cited by examiner

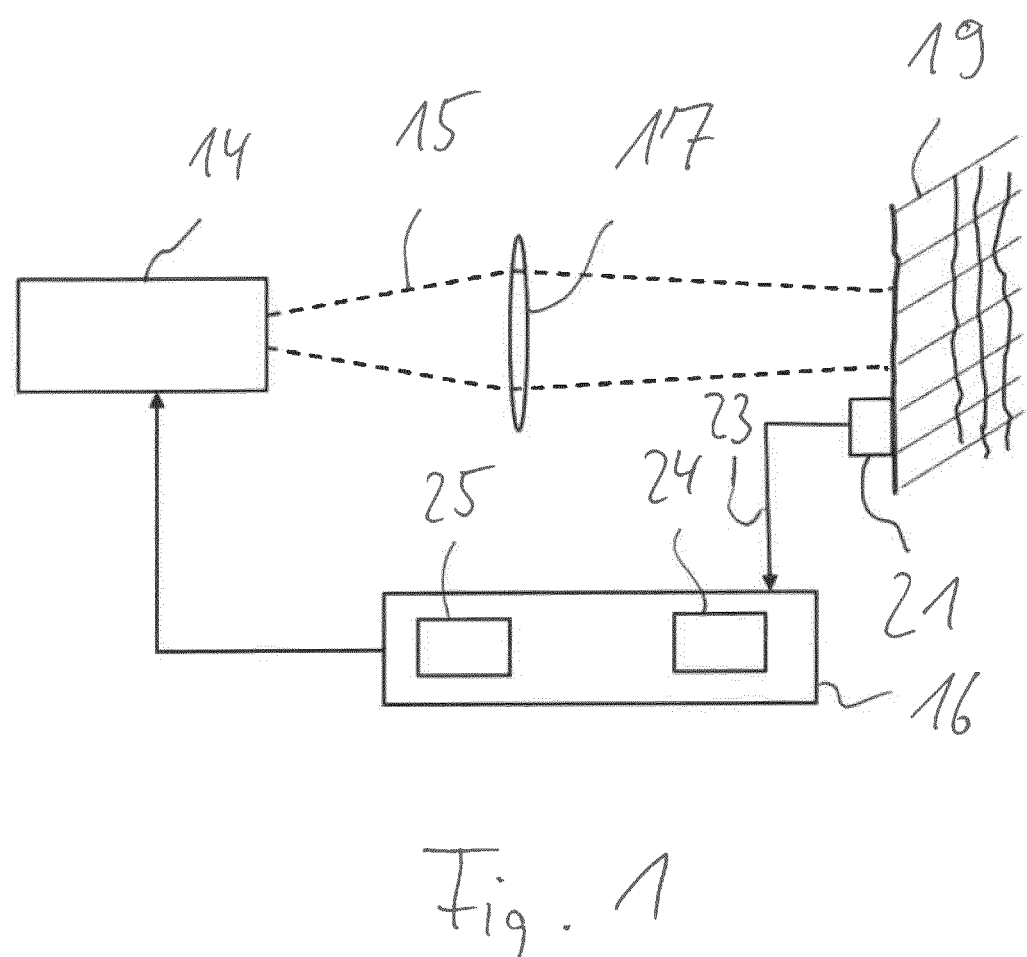
Fig. 1
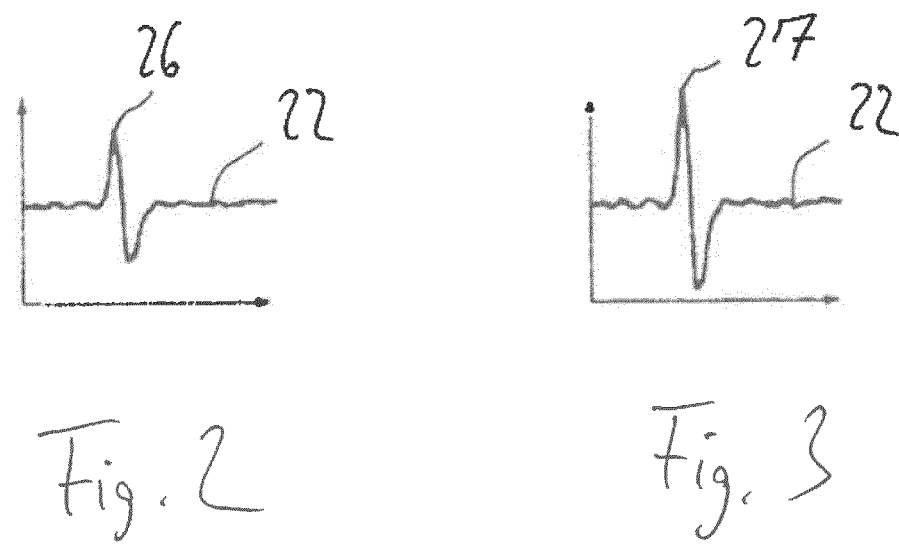
Fig. 2                           Fig. 3

DEVICE FOR TREATING BIOLOGICAL TISSUE

BACKGROUND

The invention relates to an apparatus for treating biological tissue.

A therapeutic effect is known to be able to be produced if tissue is set to vibrate at a frequency of vibration in the ultrasonic range. This, and much else, was described for nervous cells in Teudt et al., IEEE T Bio-med Eng 58(6) 2011 and for auditory nerves of the cochlea in Wenzel et al., JBO 14(4) 2009.

Tissue can be set to vibrate by acting on the tissue with repeating light pulses, the latter being absorbed by the tissue. The light pulses trigger a thermoplastic expansion and subsequent contraction and are therefore able to be used to excite the vibration. To date, it was found to be not quite straightforward to adjust the light source such that the desired effects are produced in the biological tissue without this damaging the tissue. How intensively the tissue reacts to light pulses depends on the type and state of the tissue and on the amplitude and frequency of the vibration. For tissue responding intensely to the light pulses, there is the risk of the tissue becoming permanently damaged as a result of an amplitude that is too high if the light pulses are too strong. In the case of less sensitive tissue, it may be the case that the desired effects are not produced if the light pulses are too weak or the amplitudes are too low.

SUMMARY

The invention is based on the object of developing an apparatus for treating biological tissue, wherein the tissue can be treated using pulsed light so that a desired vibration state of the tissue is reliably produced. Proceeding from the aforementioned prior art, this object is achieved by the features of the independent claim. Advantageous embodiments are specified in the dependent claims.

The apparatus according to the invention comprises a light source in order to send a large number of light pulses onto the tissue within a treatment time period, so that the tissue is set vibrating. The apparatus also comprises a vibration sensor, which measures the amplitude of a vibration of the tissue triggered by the light source. A relative value is formed in a control unit by virtue of a current measured value of the amplitude being related to an initial measured value of the amplitude. The relative value is processed in the control unit in order to generate a control signal for the light source.

The invention is based on the concept of controlling the light source on the basis of a control signal which was determined on the basis of an actual vibration of the tissue triggered by a light pulse. The light source is therefore no longer adjusted on the basis of assumptions, made in advance, about the effect of the light pulses on the tissue; instead, a control signal that depends on the actual vibration of the tissue is generated for the light source. This provides the option of adjusting the light source in a targeted manner so that specific vibration states are produced in the tissue.

It was recognized that the absolute value of the measured amplitude per se does not always represent a suitable criterion for controlling the light source. Therefore, the invention includes the proposal of relating a current measured value of the amplitude to an initial measured value of the amplitude. The initial measured value recorded at the start of the treatment period specifies how the tissue reacts to the light pulses at the start of the treatment. The ratio between the current measured value and the initial measured value of the amplitude forms a measure that is related to the extent to which the tissue is made to vibrate. This information is processed, in the form of the relative value, in the control unit in order to control the further course of the treatment with light pulses.

The amplitude of the tissue vibration depends on the pulse energy; the higher the pulse energy, the greater the amplitude. If the amplitude of the tissue vibration increases despite the pulse energy remaining the same, then this indicates a stronger vibration.

The initial measured value of the amplitude and the current measured value of the amplitude can be normalized to the pulse energy, so that the relative value is a normalized relative value. Whether the amplitude of the tissue vibration has changed in relation to the same pulse energy can be read from the normalized relative value. The relative value is automatically a normalized relative value within this meaning if light pulses with identical pulse energy are sent onto the tissue.

The treatment with the apparatus according to the invention does not serve to bring about a permanent structural change in the tissue. Instead, the tissue should be excited or stimulated by the vibration without the said tissue being damaged in terms of its structure. If the amplitude increase is too great, then there is a risk of mechanical damage to the tissue due to tearing of the structures or thermal damage due to a now insufficient dissipation of the arising heat. It is therefore possible to predefine a limit value for the relative value, and the light source can be controlled so that the relative value does not exceed the limit value. For example, that limit value can have a value of between 1.1 and 2, preferably between 1.3 and 1.6.

It is also possible to predefine a target value for the relative value and control the light source so that the relative value reaches the target value. The treatment can be terminated when the target value is reached, which is to say the light source can be controlled so that it no longer emits any light pulses. It is also possible to control the light source so that the relative value remains at the target value for a predefined time interval. Other variants are also possible, for example that the treatment is continued at a lower relative value after the target value has been reached. By way of example, this can be achieved by virtue of the pulse energy or pulse duration of the light source being reduced and/or the time interval between two successive pulses being increased. For example, the target value for the relative value can lie between 1.05 and 1.5, preferably between 1.1 and 1.3, more preferably between 1.15 and 1.25.

In an embodiment, a characteristic curve over time is predefined for the relative value and the light source is controlled so that the relative value follows the characteristic curve.

The light source can be controlled so that light pulses are emitted with constant energy. The time interval between the light pulses may stay the same during a treatment. However, it is also possible to modify the time interval within a treatment in order to influence the progress of the tissue vibration.

In a different embodiment, a low-energy light pulse is sent onto the tissue at the start of the treatment, with the energy being dimensioned so that damage to the tissue is reliably precluded. The pulse energy can be increased over the course of the treatment until a desired vibration state of the tissue has been produced. Using the normalized relative value, it is possible to ensure that the amplitude does not increase to such an extent that the tissue is damaged.

The apparatus may comprise a closed control loop, which controls the emission of the light pulses in such a way that the vibration of the tissue is set to a predefined amplitude. By way of example, it may be desirable for the amplitude to be kept at a constant setpoint value following an increase at the start of the treatment. The control signal for the light source can be designed so that the constant setpoint value is produced.

It is also possible that a characteristic curve for the amplitude of the tissue vibration is predefined and that the light source is controlled by way of the closed control loop so that the amplitude is set in accordance with the predefined characteristic curve. By way of example, a characteristic curve for a predefined increase or decrease of the amplitude measured values over time may be predefined at the start of the treatment or during a time interval of the treatment. The resultant control of the course of the treatment can be implemented in addition or as an alternative to the control in relation to the relative value.

The light source can be configured so that a large number of similar light pulses are directed at the tissue for the duration of a treatment. The light pulses may have the same pulse duration. The light pulses may have the same pulse energy, with the result that the same quantity of energy is transferred to the tissue with each light pulse. A treatment with differing light pulses for the purpose of an adjustment to the vibration of the tissue is also possible, wherein in particular the pulse duration and/or the pulse energy and/or the pulse repetition frequency are able to be adjustably controlled by a control unit over the duration of a treatment. By way of example, the duration of an individual light pulse can be between 0.1 ns and 100 µs, preferably between 10 ns and 2 µs.

The wavelength of the light may comprise one, two or more than two spectral ranges which are absorbed by the tissue to different extents in order to excite the tissue to vibrate to different extents in different portions. The light source may be a laser light source which emits light in a tightly delimited spectral range. In this case, the various spectral ranges may comprise the entire spectrum from UV to the far IR spectrum, and may for example range between 300 nm and 3000 nm. Specific embodiments may contain for example a laser with an emission at the fundamental frequency and the frequency-doubled component thereof, for example 1064 nm and 532 nm. Pulses of different wavelength can be mixed synchronously or asynchronously in any desired sequence. A preferred variant for exciting vibrations is an alternating emission of light pulses, with the light pulses lying in different spectral ranges. The temporal pulse spacing may be the same.

The light pulses can be emitted in such a way that the duration of a light pulse is shorter than the time interval between the end of a first light pulse and the start of a second light pulse immediately following the first. Preferably, the duration of a pause between two successive light pulses is longer than the pulse duration by at least a factor of 10, preferably by a factor of 100, more preferably by a factor of 1000.

The pause between two light pulses should not be so long that the tissue vibration decay back to the initial state during this time. Rather, what is sought after is that the tissue is excited into a continuous vibration by the sum of the introduced light pulses. Therefore, the interval between the pulses should preferably be shorter than the thermal relaxation time of the excited tissue.

A treatment refers to a sequence of light pulses which, overall, bring about a continuous vibration treatment of the tissue. If another light pulse is directed at the tissue after the tissue has returned to its initial state in the meantime, then this is the start of a new treatment. The time a treatment takes is referred to as the treatment time period.

The invention also comprises an apparatus configured so that light pulses in the form of therapy pulses and light pulses in the form of measurement pulses are directed at the tissue within the treatment time period. The therapy pulses may have a different spatial extent to the measurement pulses. A different spatial extent means that the area covered on the treated tissue is larger or smaller. In particular, the area covered by the therapy pulses may be larger than the area covered by the measurement pulses. By way of example, the measurement pulse can be placed in the center of the treatment area in order to record the maximum amplitude of the tissue vibration. In addition or as an alternative to the different spatial extent, the measurement pulses and the therapy pulses may also have different pulse durations and/or pulse repetition frequencies.

The control unit can be configured so that, for the purpose of controlling the light source, it processes only amplitude measured values of vibrations of the tissue triggered by measurement pulses. One or more therapy pulses, the pulse duration and pulse energy of which is oriented to the requirements of the treatment, may in each case be bookended by two measurement pulses.

The apparatus may comprise a measurement light source to produce the measurement pulses, which is separate from the light source used for the tissue treatment. The measurement pulses can lie in a different spectral range from the therapy pulses. It is also possible for the measurement pulses and the therapy pulses to be produced by a uniform light source.

The light source can be a laser light source. The beam path of the light source can be shaped so that a spot on the tissue is illuminated. The spot size, which is to say the diameter of the spot, can be chosen on the basis of the treated tissue. If the retina of the eye is treated, the spot size can lie between 50 µm and 500 µm, preferably between 100 µm and 200 µm. In the case of the tympanum of the ear, the spot can have a size of 5 mm, for example. In the case of other tissues such as subcutaneous nervous tissue, for example, it is possible to work with other spot sizes that depend on the size of the treatment area, for example spot sizes between 2 mm and 20 mm, preferably between 3 mm and 8 mm.

The radiant exposure of an individual light pulse can lie between 0.1 and 100 mJ/cm², for example, and may more preferably be less than the maximum radiant exposure of tissue specified in accordance with the European standard DIN-EN 60825-1. The duration of a single treatment can be between 0.02 s and 100 s, preferably between 0.05 s and 10 s, more preferably between 0.1 s and 1 s. However, a permanent vibration excitation, for example for the modulated excitation of the tympanum, middle ear or inner ear, is also conceivable. The number of light pulses during a treatment can lie between 100 and 100 000. A treatment refers to a sequence of light pulses which, overall, bring about a continuous vibration treatment of the tissue. If another light pulse is directed at the tissue after the tissue has returned to its initial state in the meantime, then this is the start of a new treatment. All light pulses during a treatment can be directed at the same region of the tissue.

The vibration of the tissue triggered by a light pulse can be a thermoplastic expansion and contraction. The vibration sensor can be designed for a direct measurement of the tissue expansion. By way of example, this is possible if the vibration sensor is an optical or acoustic interferometer.

It is also possible to use the vibration sensor to measure the acoustic wave emitted during the vibration, its amplitude and/or its spectrum, and to draw conclusions about the vibration state of the tissue in this way. The vibration sensor may comprise a microphone, hydrophone or a piezo element, which reacts to the pressure wave.

BRIEF DESCRIPTION OF THE DRAWINGS

The invention is described in exemplary fashion on the basis of advantageous embodiments hereinafter, with reference being made to the attached drawings. In the latter:

FIG. 1 shows an embodiment of an apparatus according to the invention;

FIG. 2 shows the curve of the vibration triggered by a light pulse at the start of a treatment;

FIG. 3 shows the view of FIG. 2 during a later stage of the treatment;

DETAILED DESCRIPTION

Figures 4, 5:
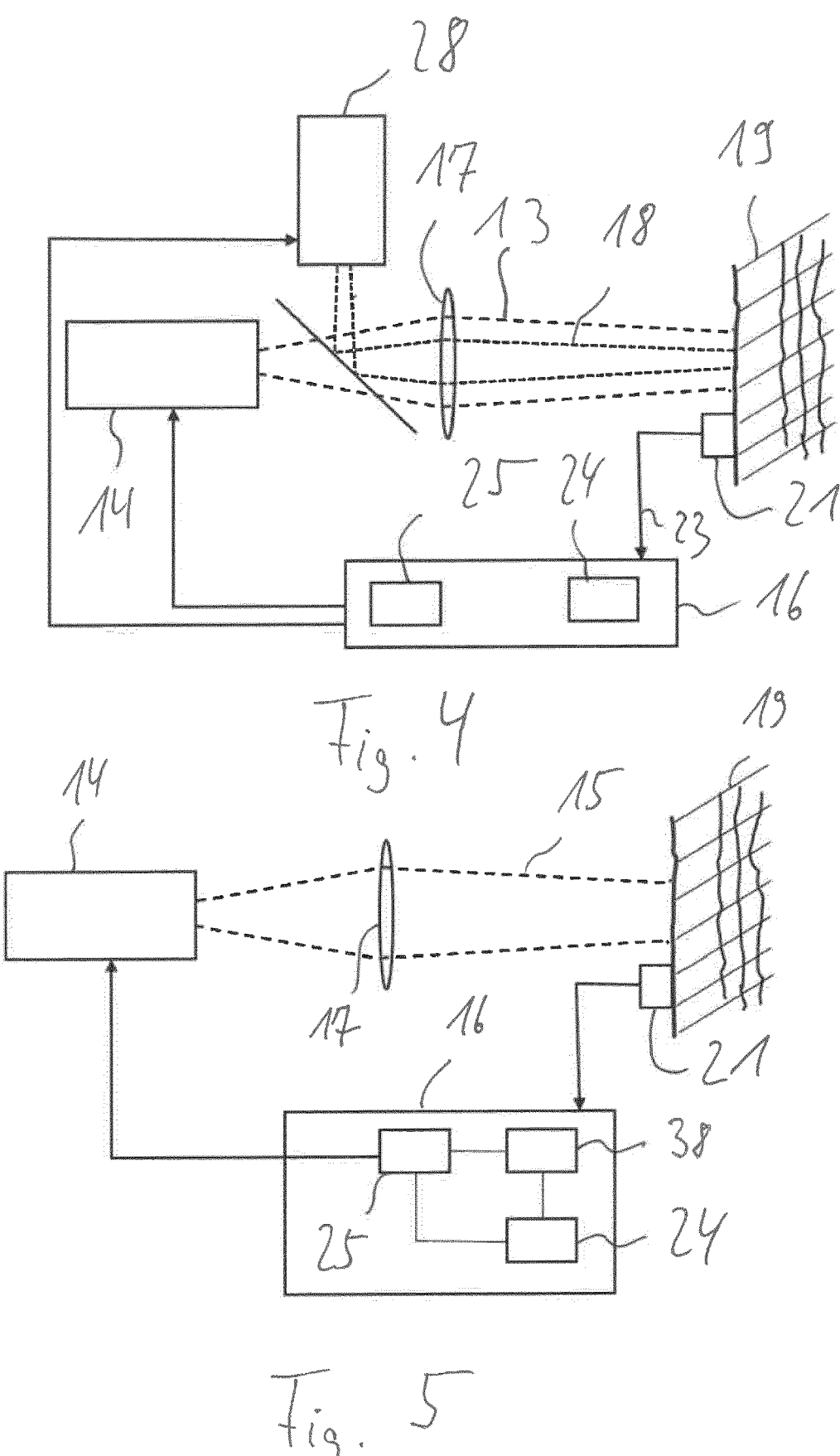
FIGS. 4-6 show alternative embodiments of apparatuses according to the invention.

An apparatus according to the invention shown in FIG. 1 comprises a laser light source 14 which, under the control of a control unit 16, emits light pulses 15 of at least one wavelength. The light pulses 15 are guided by suitable optical elements 17 to nervous tissue 19 of a patient. Each light pulse 15 induces a vibration in the form of a thermoplastic expansion in the retinal tissue. The vibration triggers a pressure wave 22 which propagates starting from the nervous tissue 19. FIGS. 2 and 3 show exemplary curves of the pressure wave over time.

The apparatus comprises a vibration sensor 21 in the form of a hydrophone. The vibration sensor 21 reacts to the pressure wave 22 and emits an electrical signal which represents the amplitude and the frequency of the pressure wave 22. The amplitude of the pressure wave 22 corresponds to the amplitude of the vibration of the nervous tissue 19.

The electrical signal generated by the vibration sensor 21 is sent as an amplitude measured value to the control unit 16 via a line 23 and is processed in the control unit 16. A first light pulse 15 is sent onto the nervous tissue 19 at the start of a treatment, resulting in the triggering of a first pressure wave 22, the amplitude of which is shown in FIG. 2. The profile of the pressure wave 22 is registered using the vibration sensor 21. The associated amplitude measured value is stored in a memory 24 as the initial measured value 26 of the amplitude.

Figures 6, 7:
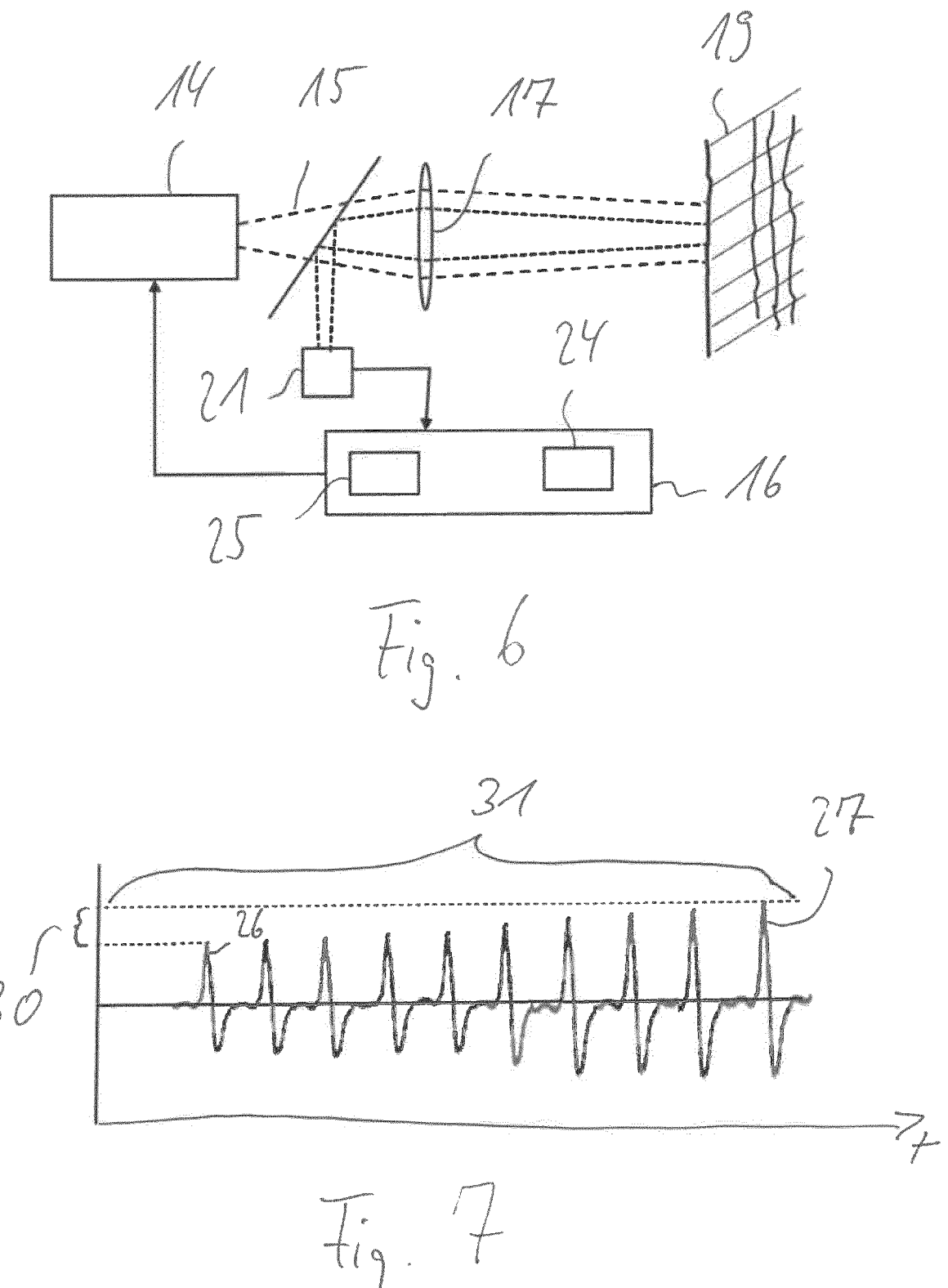
FIG. 7 shows the amplitude of the tissue vibration over the course of a treatment.

Further similar light pulses 15 are guided to the nervous tissue 19 at constant intervals over the course of the treatment. Each light pulse 15 brings about a new excitation of the vibration of the nervous tissue 19. The vibrations of the nervous tissue 19 decay in the pause between two light pulses 15 without fully decaying. Overall, the light pulses 15 lead to a continuous vibration excitation of the nervous tissue 19. FIG. 7 shows the time profile of a treatment in exemplary fashion, with the horizontal axis showing the time t and the vertical axis showing the amplitude of the tissue vibration. The relative value 30 according to the invention is determined by virtue of a current measured value of the amplitude being related to the initial measured value 26 of the amplitude. The interval between the light pulses is such that the tissue vibrations never decay completely during the treatment time period 31.

The amplitude of the pressure wave 22 increases as a result of the permanent excitation with similar light pulses 15. FIG. 3 depicts the pressure wave 22 at the end of the treatment shown in FIG. 5. The amplitude measured value 27 is 50% greater than the initial measured value 26 of the amplitude.

All amplitude measured values 27 obtained during the treatment are guided to the control unit 16, where a relative value is formed by virtue of each amplitude measured value 27 being related to the initial measured value 26 of the amplitude stored in the memory 24. The relative value is compared with a limit value in a comparator 25 of the control unit 16. The control unit 16 sends a deactivation signal to the light source 14 as soon as the relative value reaches the limit value, with the result that the light source 14 no longer emits any light pulses 15. The limit value for the ratio between the amplitude measured value and the initial measured value 26 of the amplitude (relative value) is 1.5 in the exemplary embodiment; the limit value is thus reached once the amplitude measured value 27 is 50% higher than the initial measured value 26 of the amplitude. In FIG. 7, the treatment is terminated once the limit value is reached. Subsequently, the nervous tissue readopts its initial state without vibrations.

In the exemplary embodiment according to FIG. 4, the light source 14 preferably does not emit similar light pulses 15; instead, the pulse energy and/or the intervals change over the duration of the treatment. The apparatus comprises an additional measurement light source 28, which guides measurement pulses 18 to the nervous tissue 19 during the pauses between the therapy pulses 13 emitted by the light source 14. On the nervous tissue 19, the therapy pulses 13 cover a greater area than the measurement pulses 18. Only the pressure waves triggered by the measurement pulses 18 are evaluated in the control unit 16, and only these are related to the initial measured value 26 of the amplitude, which is likewise obtained using the measurement pulse 18. In this way, the progress of the therapy pulses 13 can be aligned with the needs of the treatment without the measurement with the measurement pulses 18 being impaired. After a target value for the amplitude has been reached, the pulse energy of the therapy pulses 13 is reduced so that the amplitude of the vibrations of the nervous tissue 19 remains constant for the remaining duration of the treatment.

The light pulses 15 are likewise varied over the duration of the treatment in the embodiment according to FIG. 5. The memory 24 of the control unit 16 is used to store not only the initial measured value 26 of the amplitude but also the pulse energy of the first light pulse 15 which triggered the relevant pressure wave 22. Subsequent pressure waves are triggered by light pulses 15 that have a different pulse energy, pulse duration and/or pulse repetition rate. Before the amplitude value 27 is supplied to the comparator 25 for the purpose of the comparison with the initial measured value 26 of the amplitude, the amplitude value 27 is normalized to the pulse energy in the component 38. A normalized relative value is generated and reproduces the ratio, normalized to the pulse energy, of the amplitude value 27 to the initial measured value 26 and represents a change in the state of the nervous tissue 19.

FIG. 6 illustrates an alternative embodiment, in which the amplitude of the tissue vibration is measured using a vibration sensor 21 in the form of an optical sensor.

The invention claimed is:

1. An apparatus for treating biological tissue (19), said apparatus comprising:

a light source (14) configured to send a number of light pulses (15) onto the tissue (19) within a treatment time period (31), so that the tissue (19) vibrates;

a vibration sensor (21), which measures an amplitude of the vibration (22) of the tissue (19) triggered by the light pulses (15); and a control unit (16), which forms a relative value (30) by virtue of a current measured value (27) of the amplitude being related to an initial measured value (26) of the amplitude, and which processes the relative value (30) to generate a control signal for the light source (14).

2. The apparatus of claim 1, wherein the initial measured value (26) of the amplitude and the current measured value (27) of the amplitude are normalized to a pulse energy, so that the relative value (30) is a normalized relative value.

3. The apparatus of claim 1, wherein a target value for the relative value (30) is predefined, and in that the control unit (16) controls the light source (14) so that the relative value (30) reaches the target value.

4. The apparatus of claim 3, wherein the target value lies between 1.05 and 1.5.

5. The apparatus of claim 1, wherein a characteristic curve over time is predefined for the relative value (30), and in that the control unit (16) controls the light source (14) so that the relative value (30) follows the characteristic curve.

6. The apparatus of claim 1, wherein the control signal is integrated in a closed control loop, with which the relative value is set to a predefined target value or a predefined time profile.

7. The apparatus of claim 1, wherein a duration of a pause between two successive light pulses is shorter than a relaxation time of the tissue.

8. The apparatus of claim 1, wherein the light pulses (15) form a spot on the tissue, wherein the spot has a diameter between 0.1 mm and 10 mm.

9. The apparatus of claim 1, wherein the light source (14) is configured to direct light pulses of different spectral ranges at the tissue.

10. The apparatus of claim 1, wherein the light source (14) is configured to send onto the tissue, within the treatment time period (31), light pulses (15) in the form of measurement pulses (18) and light pulses (15) in the form of therapy pulses (13), wherein the vibration sensor (21) measures the amplitude of the tissue vibration triggered by the measurement pulses (18) and these measured values are processed in the control unit (16).

11. The apparatus of claim 10, wherein the therapy pulses (13) cover a larger area on the tissue (19) than the measurement pulses (18).

12. The apparatus of claim 10, wherein the therapy pulses (13) are output in a different spectral range from the measurement pulses (18).

13. The apparatus of claim 1, wherein the number of light pulses (15) during a treatment lies between 100 and 100 000.

14. The apparatus of claim 1, wherein the vibration sensor (21) determines the amplitude of the initial measured value (26) or the amplitude of the current measured value (27) by using a pressure wave (22) triggered by the vibration of the tissue (19).

15. The apparatus of claim 1, wherein the vibration sensor (21) determines the amplitude of the tissue vibration optically by means of an interferometer.

* * * * *